(12) United States Patent
Van Damme et al.

(10) Patent No.: US 7,419,778 B2
(45) Date of Patent: Sep. 2, 2008

(54) METHOD FOR HIGH THROUGHPUT CELL-BASED ASSAYS USING VERSATILE LIVING MICROARRAYS

(75) Inventors: Hendrik Sibolt Van Damme, Den Bosch (NL); Herman Jacobus Blok, Retie (BE); Maria Helena Hilhorst, Wageningen (NL); Colin John Ingham, Den Bosch (NL)

(73) Assignee: PameGene B.V., Den Bosch (NL)

( * ) Notice: Subject to any disclaimer, the term of this patent is extended or adjusted under 35 U.S.C. 154(b) by 480 days.

(21) Appl. No.: 10/516,473

(22) PCT Filed: Jun. 3, 2003

(86) PCT No.: PCT/EP03/05798

§ 371 (c)(1),
(2), (4) Date: Nov. 30, 2004

(87) PCT Pub. No.: WO03/102578

PCT Pub. Date: Dec. 11, 2003

(65) Prior Publication Data

US 2005/0255445 A1 Nov. 17, 2005

(30) Foreign Application Priority Data

Jun. 3, 2002 (EP) .................. 02447105

(51) Int. Cl.
*C12Q 1/00* (2006.01)
*C12M 1/34* (2006.01)
*C12M 1/00* (2006.01)

(52) U.S. Cl. ............... 435/4; 435/287.1; 435/289.1

(58) Field of Classification Search .............. None
See application file for complete search history.

(56) References Cited

U.S. PATENT DOCUMENTS

| | | | |
|---|---|---|---|
| 6,103,479 A | 8/2000 | Taylor | |
| 6,197,575 B1 | 3/2001 | Tannenbaum et al. | |
| 6,225,131 B1 | 5/2001 | van Damme et al. | |
| 2002/0072116 A1* | 6/2002 | Bhatia et al. ............. | 435/366 |
| 2007/0072187 A1 | 3/2007 | Blok et al. | |

FOREIGN PATENT DOCUMENTS

| | | |
|---|---|---|
| WO | WO 98/38490 | 9/1998 |
| WO | WO 99 02266 | 1/1999 |
| WO | WO 00 31304 A | 6/2000 |
| WO | WO 00 63701 A | 10/2000 |
| WO | WO 01/020015 | 3/2001 |
| WO | WO 01/45843 A2 | 6/2001 |

OTHER PUBLICATIONS

Smith et al. The Analysis of Doxorubicin Resistance in Human Breast Cancer Cells Using Antibody Microarrays; Molecular CAncer Therapeutics, vol. 5, No. 8 (2006) pp. 2115-2120.*
Tanaka et al. Drug Response Assay System in a Microchip Using Human Hepatoma Cells; Analytical Sciences, vol. 20 (2004) pp. 411-413.*
Sambrook, et al. "Molecular Cloning: A Laboratory Manual," 3rd Edition, Cold Spring Harbor Laboratory Press, 2001, pp. 1.126-1.134.
Tobery, et al., "A Simple and Efficient Method for the Monitoring of Antigen-Specific T Cell Responses Using Peptide Pool Arrays in a Modified ELISpot Assay," Journal of Immunological Methods, vol. 254, No. 1-2, Aug. 1, 2001, pp. 59-66.
Lin, et al., "Cholera Toxin-Induced Moducation of Gene Expression: Elucidation via cDNA Microarray for Rational Cell-Based Sensor Design," Analytica Chimica Acta, vol. 457, No. 1, 2002, pp. 97-108.
The Japanese Biochemical Society, entitled "New Biochemical Experimental Course 1 Protein I-Separation, Purification and Property," 1990, pp. 399-403.
The Japanese Biochemical Society, entitled "New Biochemical Experimental Course 2 Nucleic-acid II-Structure and Property," 1991, pp. 197-209.

* cited by examiner

*Primary Examiner*—Jon P Weber
*Assistant Examiner*—Paul C. Martin
(74) *Attorney, Agent, or Firm*—Amster, Rothstein & Ebenstein LLP

(57) ABSTRACT

The present invention relates to methods for screening of cellular responses of cellular components comprising: (a) providing cellular components on the surface of a substrate, said substrate having immobilized thereon an array of detector molecules; (b) delivering test compounds to positions on the substrate corresponding to the arrayed detector molecules on the surface of said solid substrate; (c) incubating said test compounds with said cellular components on the surface of the solid support, under conditions allowing the induction of cellular responses; (d) assaying said cellular responses; and, identifying and characterizing the cellular responses induced by said test compounds. The present invention further relates to the uses of said methods as well as microarrays and kits for carrying out said methods.

31 Claims, 10 Drawing Sheets

A

B

C

METHOD FOR HIGH THROUGHPUT CELL-BASED ASSAYS USING VERSATILE LIVING MICROARRAYS

This application is a U.S. National Phase of PCT Application No. PCT/EP03/05798, filed Jun. 3, 2003 and claims priority to European Application No. 02447105.4, filed Jun. 3, 2002.

FIELD OF THE INVENTION

The present invention relates to cell-based assays. The present invention relates to a method for on-chip functional screening assays of cellular responses. The present invention relates to a method for screening and pharmacological profiling of compounds modulating a cellular physiological response.

BACKGROUND TO THE INVENTION

Within the pharmaceutical industry, there is a significant number of compounds, available in compound repositories, through the use of combinatorial chemistry. Hits from these compound libraries are identified through the use of high throughput screening (HTS). The primary function of HTS is to test various chemical compounds from a compound repository against multiple disease targets in many different biological assays. Traditional HTS commonly utilizes 96-well microtiter plates. There is a large incentive in the pharmaceutical industry to miniaturize these microplate assays to reduce cost, reduce waste, and speed up timelines. There has been a change from the 96-well format to higher well densities such as 384- and 1536-well formats, however these can present challenges in relation to liquid handling, signal detection instrumentation, and assay technology. In addition, typical difficulties encountered when using microtiter plate based screening assays include e.g. (i) differential growth and/or gene expression of identical clones in separate wells of the microtiter plate and (ii) differential stress exposure (e.g. heat treatment, humidity) across the plate.

Efforts have been made towards resolving the aforementioned difficulties. For example, WO 99/35496 provides a method and apparatus for high density format screening for bioactive molecules with a much simplified technique for test compound delivery to a layer of cells, i.e. without the need of complicated fluid handling. In the said method, up to 6144 test compounds may be simultaneously screened for bioactivity.

Nevertheless, there is a need for even higher density cell-based functional biological assays which remain one of the most difficult types of assays to miniaturize due to the limitations of delivering microliter quantities of cells consistently without shearing the cells or activating stress responses of the cells themselves, therefore interfering with the biological assay.

With the advent of combinatorial chemistry approaches to identify pharmacologically useful compounds, it is increasingly evident that there is a need for methods and apparatuses at microarray levels, capable of performing high throughput characterization of pharmacological profiles and corresponding potencies of the compounds in synthesized combinatorial libraries.

Microarrays of living cells could provide a shortcut to the development of safer and more customized personal drugs and a better understanding of the molecular pathways encountered in the functioning of cellular organisms. As an example, the Whitehead Institute for Biomedical Research in Cambridge developed microarrays of living cells for high-throughput analysis of gene function in mammalian cells (Nature, Vol. 411, 3 May 2001). While said technology is highly effective, there are, however, a number of limitations to its use including, the relative high reagent quantities needed of which a substantial amount is never in contact with the array and is therefore wasted, and the requirement of cumbersome and time-consuming handlings.

U.S. Pat. No. 6,103,479 discloses a further example of a microarray of living cells. The disclosed miniaturized cell arrays characterized by a reduced well and array size allow for high content screening. The non-porous character, however, does not allow the cells growing in/on the wells or cell binding sites on the array to overcome spreading under standard growth conditions which obviously interferes with proper cell sample discrimination.

As will be appreciated in the art, there is a continuous need for improved methods which overcome the aforementioned disadvantages.

It is therefore an object of the present invention to provide a highly efficient and cost-effective method for integrated cell-based assays using microarrays.

It is a further object of the present invention to provide a method for high-throughput cell-based assays requiring minimal amounts of sample and reagents.

It is also an object of the present invention to provide microarrays or kits to perform such methods.

SUMMARY OF THE INVENTION

The present invention relates to a method for screening cellular responses of cellular components comprising:
  (a) providing cellular components on the surface of a substrate, said substrate having immobilized thereon an array of detector molecules;
  (b) delivering test compounds to positions on the substrate corresponding to the arrayed detector molecules on the surface of said solid substrate;
  (c) incubating said test compounds with said cellular components on the surface of the solid support, under conditions allowing the induction of cellular responses;
  (d) assaying said cellular responses; and,
  (e) identifying and characterizing the cellular responses induced by said test compounds.

The present invention further discloses uses of the above method according to the invention.

The present invention provides for a miniaturization to microarray format of cell-based assays, thereby increasing throughput, while decreasing the volumes of reagents and test compounds.

Due to the flow-through characteristics of the device used in said method, the present method further provides for high speed and efficient analysis.

The method according to the invention allows for a non-invasive on-chip culturing of cells or cellular components, said layer growing under equal conditions across the surface of the solid substrate, and said cells or cellular components being in contact with the culturing medium only for the time necessary to obtain a desired density.

Additional features and advantages of the invention will be set forth in the detailed description which follows, and in part will be apparent from the description, or may be learned by practice of the invention. The objectives and other advantages of the invention will be realized and attained by the process particularly pointed out in the written description and appended claims.

DETAILED DESCRIPTION OF THE INVENTION

Before the present method and solutions used in the method are described, it is to be understood that this invention is not limited to particular methods, components, or solutions described, as such methods, components, and solutions may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

Performing a screen on many thousands of compounds requires parallel handling and processing of many compounds and assay component reagents. Standard high throughput screens use mixtures of compounds and biological reagents along with some indicator compound loaded into arrays of wells in standard microtiter plates.

The present invention relates to a large-scale miniaturization comprising use of a solid substrate to which a multitude of molecules are attached in predefined regions to form a microarray.

There are mainly three different components involved in the cellular arrays according to the present invention: cellular components, test compounds and detector molecules. In addition, cell-capturing molecules may be involved as a fourth component; these may be for example antibodies to capture a specific bacterium each. Depending on the nature of the capture molecules, specific cells (bacteria, fungi, viruses, mycoplasmas) may be captured. A variety of distinct capture molecules on an array may provide for a cellular array comprising a variety of distinct cellular components. The present invention provides a versatile integrated cellular-based assay wherein a number of test formats are envisaged.

In an array of cellular components, islands of different cells are grown or deposited on the substrate in an array format. Subsequently the whole array is exposed to one (or a limited number) of test compounds and finally exposed to one (or a limited number) of receptor molecules (possibly present in the substrate) if necessary after lyses. As such, this test format allows the screening of an array of different cellular components for responses induced by a particular test compound, detected with a particular detector molecule. Said detector molecule may be provided subsequent to the incubation of the test compound with the cellular compounds or may have been introduced within the substrate prior to contact of the substrate with the cellular components. In addition, a detector molecule may have been introduced into the cellular components prior to exposure to the test compounds; e.g. GFP may be expressed as a cellular response.

Cellular components may be captured on the solid substrate by capture molecules which were previously deposited onto said solid substrate.

The terms "detector molecule", "receptor molecule" and "discriminator molecules" may be used interchangeable and refer, in the context of the present invention, to molecules which allow the detection of a cellular response. A detector molecule may also be generated by the conversion of a test compound.

In a test substance array a homogeneous layer of a cellular component is locally, at predefined regions, treated, by spotting, with various test substances. Also, the test substance or test compound may be present in the substrate before the cellular components are applied or the test substance or test compound may be present in the cells. After treatment, cellular responses may be detected with a particular detector molecule. Said detector molecule may be provided subsequent to the incubation of the test compound with the cellular compounds or may have been introduced within the substrate prior to contact of the substrate with the cellular components. Also, the detector molecule may have been introduced in the cells such as for example to obtain GFP-expressing cells.

In a detector array, an array of different receptor or detector molecules are contacted with a homogeneous layer of cellular components which are treated with a particular test compound (or a few after each other). Cellular responses are monitored by detecting excretion products by the receptor molecules or by detecting intracellular products through binding to the receptor molecules after lysis of the cellular components. Cell death and morphological changes may also be detected.

The nature and geometry of the solid substrate will depend upon a variety of factors, including, among others, the type of array and the mode of attachment. Generally, the substrate may be composed of any material which will permit cell culturing and immobilization of the desired molecules and which will not melt or otherwise substantially degrade under the conditions used to perform cell-based assays. In addition, where covalent immobilization is contemplated, the substrate should be activatable with reactive groups capable of forming a bond, which may be covalent, with the molecule to be immobilized.

A number of materials suitable for use in substrates as used in the present invention have been described in the art. Exemplary suitable substrates in the present invention comprise materials including acrylic, acrylamide, methylene-bis-acrylamide, dimethylaminopropylmethacrylamide, styrenemethyl methacrylate copolymers, ethylene/acrylic acid, acrylonitrile-butadienestyrene (ABS), ABS/polycarbonate, ABS/polysulfone, ABS/polyvinyl chloride, ethylene propylene, ethylene vinyl acetate (EVA), nitrocellulose, polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), polyvinyl alcohol (PVA), silicon styreneacrylonitrile (SAN), styrene maleic anhydride (SMA), and glass. Further exemplary suitable substrates comprise mixtures of two or more of the above-mentioned materials.

Other exemplary suitable materials for the manufacture of substrates in the present invention include metal oxides. Metal oxides provide a support having both a high channel density and a high porosity, allowing high density arrays comprising different first binding substances per unit of the surface for sample application. In addition, metal oxides are highly transparent for visible light. Metal oxides are relatively cheap substrates that do not require the use of any typical microfabricaton technology and, that offer an improved control over the liquid distribution over the surface of the substrate, such as electrochemically manufactured metal oxide membrane. Metal oxide membranes having through-going, oriented channels may be manufactured through electrochemical etching of a metal sheet. Metal oxides considered are, among others, oxides of tantalum, titanium, and aluminum, as well as alloys of two or more metal oxides and doped metal oxides and alloys containing metal oxides. The metal oxide membranes are transparent, especially if wet, which allows for assays using various optical techniques. Such membranes have oriented through-going channels with well-controlled diameter and useful chemical surface properties. WO 99/02266, which describes the use of Anopore™, is exemplary in this respect, and is specifically incorporated in the present invention.

Accordingly, in one embodiment of the present invention, the solid substrate is a porous solid support.

In a further embodiment, the solid substrate as comprised in the steps of the method of the present invention is a flow-through solid support.

In a further embodiment, the solid substrate as comprised in the steps of the method of the present invention is a metallo-oxide substrate.

In a further embodiment, the solid substrate as comprised in the steps of the method of the present invention is an aluminum-oxide substrate.

The term "cellular components" as used throughout the present specification refers to whole intact viable cells including, e.g. prokaryotic cells; as well as cell components such as vesicles, organelles and vectors; as well as sectioned material such as tissue sections; as well as fixed cells; as well as microscopic multicellular organisms such as, e.g., nematodes, zebrafish; and others. Cellular components may be also viruses, bacteria and mycoplasmas.

According to the present invention, the surface of said solid substrate may be contacted, by direct deposit thereon, with an inoculum of cellular components. Said inoculum may be a liquid formulation comprising said components and an appropriate growth medium.

The final inoculum, however, may also be disposed of any growth medium and comprise preservers instead such as glycerol (e.g. bacterial cultures). Accordingly, cellular components may be preserved on the substrate for analysis later on; i.e. cellular components may be on the substrate under preserving conditions such as in glycerol or other suitable medium or lyophilised. The term "preserving condition" refers to a condition to keep the cellular components alive and/or intact and free from decay.

Alternatively, a culture of cellular components may be incubated for growth until the exponential phase with respect to their growth curve is reached, followed by deposition of an aliquot of said culture directly on the substrate.

Accordingly, in one embodiment of the present invention a method is provided wherein said providing of cellular components on the surface of a substrate is by a deposit directly on said substrate of an inoculum or a culture.

As will be appreciated by a person skilled in the art, established protocols are available for the culture of diverse cell types. Such protocols may require the use of specialized coatings and selective media to enable cell growth and the expression of specialist cellular functions. None of such protocols is precluded from use with the method of the present invention.

In the present invention, nutrients may be provided to the surface of the solid substrate from underneath or from above and through the pores of said solid substrate.

Said nutrients and/or effectors may be provided by diffusion to the surface of the solid substrate from underneath or from above and through the pores of said solid substrate.

Said nutrients may be provided with a growth medium to culture the cells. Said growth medium may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art.

The provision of the nutrients to the substrate for growth of the cellular components is under aseptic conditions well-known in the art. Said aseptic conditions may be accomplished by working in a laminar flow bench or by placing a cover on the substrate; i.e. on the side of deposit or growth of the cellular components.

The method according to the present invention may also be applicable to sectioned material which may be directly positioned in contact with the substrate.

If required for downstream assays, e.g. immuno-fluorescent detection, cells may be fixed onto the surface of the solid substrate, e.g. by chemical fixation. Typically, the preferred fixative will depend upon whether the cellular response manifests or the molecule of interest is localized at the cell's surface or within the cell. For example, some fixation methods (such as methanol or acetone fixation) are not usually used on cells that will need to be permeabilized (e.g. examination of intracellular antigens).

Various fixation protocols for various cell types for various assays are well known in the art; e.g. mammalian cells may be contacted with a fixative such as phosphate-buffered saline (PBS) with 3.7% paraformaldehyde and 4.0% sucrose.

The term "cellular component" as used in the present invention encompasses any cell types that can be cultured on standard tissue culture ware. Both adherent and non-adherent cell types may be used. A "cellular component" as used in the present invention means any cell which allows the detection of a response upon exposure or treatment to/with a test compound. A cellular component according to the present specification may be a wild type, a mutant or a transformed or transfected cell (bacterial cell, viral cell, etc.) and may therefore afford the subsistence or lodgment of a non-host substance; said non-host substance may be viable such as e.g. a parasite or non-viable such as e.g. a vector and may be stably or transiently present in said host cell. A cell has been transfected by exogenous or heterologous genetic material when such material has been introduced inside the cell. A cell has been transformed by exogenous or heterologous genetic material when the transfected material effects a cellular change, e.g. a phenotypic change. Usually, the transforming genetic material should be integrated into the cell's chromosomal DNA making up its genome. Integration of transforming genetic material including vector DNA into the host chromosome may occur by homologous or non-homologous recombination. Further, a "cellular component" as used in the present specification encompasses any progeny of a parent cell which is not identical to the parent cell due to mutations that occur during replication.

Useful cells include prokaryotes and eukaryotes such as mammalian cells including hybridoma cells, insect cells, plant cells, yeast cells, and protist cells comprising protozoa, algae and fungal cells. Mammalian cells may be derived from any recognized source with respect to species (e.g. human, rodent, simian), tissue source (brain, liver, lung, heart, kidney, skin, muscle) and cell type (e.g. epithelial, endothelial). In addition, cells which have been transfected with recombinant genes may also be cultured using the present invention.

Suitable cell lines may be comprised within e.g. the American Type Culture Collection and the German Collection of Microorganisms and Cell Cultures.

In one embodiment of the present invention, the cellular components are selected from the group comprising mammalian cells, insect cells, yeast cells, plant cells, and microbial cells including bacterial and fungal cells, cellular vesicles, cellular organelles, tissue sections, and whole microscopic organisms including nematodes.

Non-limiting examples of useful mammalian cell lines include animal and human cell lines such as Chinese hamster ovary (CHO) cells, Chinese hamster lung (CHL) cells, baby hamster kidney (BHK) cells, COS cells, HeLa cells, THP cell lines, TAg Jurkat cells, hybridoma cells, carcinoma cell lines, hepatocytes and the like.

Suitable insect cell lines include but are not limited to Lepidoptera cell lines such as *Spodoptera frugiperda* cells (e.g. Sf9, Sf21) and *Trichoplusia ni* cells (e.g. High Five™, BTI-Tn-5B1-4).

Non-limiting examples of fungal cells useful in the present invention include the phyla Ascomycota, Basidiomycota, Chytridiomycota, and Zygomycota as well as the Oomycota and all mitosporic fungi. Representative groups of Ascomycota include, e.g., *Neurospora*, Eupenicillium (or *Penicillium*), *Emericella* (or *Aspergillus*), *Eurotium* (or *Aspergillus*), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., saprolegniomycetous aquatic fungi (water molds) such as *Achlya*. Examples of mitosporic fungi include *Aspergillus, Penicillium, Candiaa,* and *Altemaria*. Representative groups of Zygomycota include, e.g., *Rhizopus* and *Mucor*.

Fungal cells may be yeast cells. Non-limiting examples of useful yeast cells include ascosporogenous yeast (Endomycetales), basidiosporogenous yeast, and yeast belonging to the Fungi Imperfecti or Deuteromycota (Blastomycetes). The ascosporogenous yeasts are divided into the families Spermophthoraceae and Saccharomycetaceae. The latter is comprised of four sub-families, Schizosaccharomycoideae (e.g., genus *Schizosaccharomyces* including *S. pombe*), Nadsonioideae, Lipomyooideae, and Saccharomycoideae (e.g., genera *Pichia* including *P. pastoris, P. guillermondii* and *P. methanollo*), *Kluyveromyces* including *K. lactis, K. fragilis* and *Saccharomyces* including *S. carlsbergensis, S. cerevisiae, S. diastaticus, S. douglasii, S. kluyveri, S. norbensis* or *S. oviformis*). The basidiosporogenous yeasts include the genera *Leucosporidim, Rhodosporidium, Sporidiobolus, Filobasidium,* and *Filobasidiella*. Yeasts belonging to the Fungi Imperfecti are divided into two families, Sporobolomycetaceae (e.g., genera *Sporobolomyces* and *Bullera*) and Cryptococcaceae (e.g., genus *Candida* including *C. maltose*). Other useful yeast host cells are *Hansehula polymorpha, Yarrowia lipolytica, Ustilgo maylis*.

Fungal cells may be filamentous fungal cells including all filamentous forms of the subdivision Eumycota and Oomycota. Filamentous fungi are characterized by a vegetative mycelium composed of chitin, cellulose, glucan, chitosan, mannan, and other complex polysaccharides. Vegetative growth is by hyphal elongation and carbon catabolism is obligatory aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* and *Trichoderma* or a teleomorph or synonym thereof.

Useful microorganism cells may be unicellular, e.g. a prokaryotes, or non-unicellular, e.g. eukaryotes. Useful unicellular cells are Archeabacteria. Further useful unicellular cells are aerobic bacterial cells such as gram positive bacteria including, but not limited to, the genera *Bacillus, Sporolactobacillus, Sporocarcina, Filibacter, Caryophanum, Arthrobacter, Staphylococcus, Planococcus, Micrococcus, Mycobacterium, Nocardia, Rhodococcus*; or gram negative bacteria including, but not limited to, the genera *Acetobacter, Gluconobacter, Frateuria, Alcaligenes, Achromobacter, Deleya, Amoebobacter, Chromatium, Lamprobacter, Lamprocystis, Thiocapsa, Thiocystis, Thiodictyon, Thiopedia, Thiospirillum, Escherichia, Salmonella, Shigella, Erwinia, Enterobacter, Serratia, Legionella, Neisseria, Kingella, Eikenella, Simonsiella, Alysiella, Nitrobacter, Nitrospina, Nitrococcus, Nitrospira, Pseudomonas, Xanthomonas, Zoogloea, Fraturia, Rhizobium, Bradyrhizobium, Azorhizobium, Sinorhizobium, Rickettsia, Rochalimaea, Ehrlichia, Cowdria, Neorickettsia, Treponema, Borrelia, Vibrio, Aeromonas, Plesiomonas, Photobacterium, Brucella, Bordetella, Flavobacterium, Francisella, Chromobacterium, Janthinobacterium,* and *Iodobacter*.

Suitable plant cells for use in the present invention include dicotyledonous plant cells, examples of which are *Arabidopsis Thaliana*, tobacco, potato, tomato, and leguminous (e.g. bean, pea, soy, alfalfa) cells. It is, however, contemplated that monocotyledonous plant cells, e.g. monocotyledonous cereal plant cells such as for example rice, rye, barley and wheat, may be equally suitable.

Delivery of test compounds, cellular components or detector molecules to predefined regions on the substrate may be accomplished by using a liquid handling device but may equally be accomplished by manual handling.

Accordingly, a liquid handling device may be positioned on the substrate, wherein said liquid handling device may be a high precision x-y-z pipettor or inkjet printer containing 1 or more channels through which liquid can be dispensed, sequentially or in parallel, to positions corresponding to arrayed molecules on the surface of the solid substrate. Alternatively, a superposing mask comprising transversal holes may be superposed onto the substrate, wherein said superposing is such that each transversal hole in said mask correspond to an arrayed molecule on the surface of said solid substrate.

Superposing masks may be useful in the generation of cellular arrays; i.e. after growing a confluent layer of cells, these cells may be subsequently transformed by a set of vectors or gene-constructs to obtain an array of different transformed cells. The use of a mask during the transformation step allows the transformation of cells growing on a predefined area on the array to be transformed with a known vector or gene-construct. As such, through the use of a mask, an XY-pattern of transformed cells is created, of which the XY-position on the array identifies the transformed cells.

Delivering of test compounds, cellular components or detector molecules may be by means of contact or non-contact spotting. The term "contact spotting" or "contact force" as used in this specification means a direct surface contact between a printing substrate and a delivery mechanism that may contain one or a plurality or an array of tweezers, pins or capillaries that serve to transfer or deliver any content within the delivery mechanism to the surface by physically tapping said tweezer(s), pin(s) or capillary(ies) on the surface. Further, a superposing mask may be positioned on the (cells-containing) solid support whereby the content of the wells as formed by the filled holes in the mask is passively delivered onto said cells by capillary actions when pressing the mask onto the chip. As used in the present specification, a mask acts as a barrier to the passage of a reagent. Typically, a pattern of holes in the mask allows selective passage of reagent and results in a corresponding pattern of reagent deposition on a surface placed behind/below the mask.

Alternatively, the test compounds may also be delivered or spotted through ink-jet printing technology, a non-contact technology in which reactants are sprayed onto the surface using technology adapted from computer ink-jet printers. The ink-jet method is sometimes called indirect because the reactants are sprayed onto the surface rather than being directly placed. Ink-jet methods may be capable of producing smaller spots, and because they avoid physical contact with the surface may prove to be more reliable.

Useful ink-jet printing methodologies may include continues and drop-on-demand ink-jet methods. Most suitable ink-jet printing methods are drop-on-demand ink-jet methods, examples of which include piezoelectric and electrostatic ink-jet systems.

Further useful in the present invention are spotting robots or liquid handling devices. Most spotting robots or liquid handling devices use an X-Y-Z robot arm (one that can move in three dimensions) mounted on an anti-vibration table. Said arm may hold nozzles in case of non-contact spotting. In contact spotting, said arm may hold pins. Nozzles or pins are dipped into a first microtiter plate to pick up the fluid (e.g. test compound solution) to be delivered. The tips in case of pins are then moved to the solid support surface and allowed to touch the surface only minimally; the test compound solution is then transferred. The pins are then washed and moved to the next set of wells and test compounds. This process is repeated until hundreds or thousands of test compounds are deposited. Solid pins, quills, and pin- and- ring configurations of pins may be useful.

Accordingly, in one embodiment of the present invention, delivery of test compounds is by a means chosen from the group comprising a delivery mask, a high precision x-y-z pipettor, inkjet printer, and manual handling.

In a further embodiment of the present invention, delivery of test compounds is by a means of a high precision x-y-z pipettor or inkjet printer.

In one embodiment of the present invention, the delivery of test compounds to the cells-containing support is by means of a contact force.

In a further embodiment of the present invention, the delivery of test compounds to the cells-containing support is by means of a contact force which may be a capillary force or a piezo-electric force.

The present invention provides a method for screening and the pharmacological profiling of test compounds modulating a cellular response, e.g. a physiological response and/or the activities of cells. A variety of effects caused by the compounds to be screened may be detected and quantitatively characterized according to the present invention. These effects include but are not limited to changes in intracellular concentration of ionized calcium, CAMP differences (e.g. due to metabolic activation or inactivation), pH, temperature, NO, and transmembrane potential, intracellular Ca-, K- or Na-fluxes in or out of the cell and other physiological and biochemical characteristics of living cell which can be measured by a variety of conventional means, for example using specific fluorescent, luminescent or color developing dyes.

The present invention also includes methods of screening for agonist or antagonist activity of drugs, methods of characterizing their potency profiles, methods of identifying the receptor expression pattern of cell membrane ("receptor fingerprinting"), methods of determining toxicity profiles for the compounds (e.g. toxicological responses, CYP-450, HERC), bacterial lysis, apoptosis, cellular necrosis, cell mutation processes such as e.g. carcinogenesis, drug induced protein interactions detectable using fluorescence resonance energy transfer (FRET) or bioluminescent resonance energy transfer (BRET), ADME (adsorption, distribution, metabolism and elimination) or any other cellular responses. The plurality of cellular responses includes a cellular response selected from the group consisting of signal transduction, general protein-protein interactions, changes in enzyme activity, vesicle trafficking, protein movement, vesicle movement, activation or Inhibition of a receptor mediated response, activation or inhibition of an ion channel, activation or inhibition of a non-selective pore, activation or inhibition of a second messenger pathway at a point downstream of a receptor or channel, activation or inhibition of apoptosis, and activation or inhibition of cellular necrosis, cellular toxicity, cell differentiation and cell proliferation. Some cellular responses such as bacterial lysis, apoptosis, necrosis, proliferation do not necessarily need detector molecules for them to be detected, instead they may be detected by visual inspection.

The method of the present invention may also be used to perform biochemical analyses, such as Western analyses, Northern analyses, detection of single nucleotide polymorphisms (SNPs), detection of enzymatic activities, or molecular assembly assays.

According to the method of the present invention, the ability and potency of substances to act as agonists or antagonists against receptors, ion channels, ion pumps, and ion transporters localized on a cell surface membrane may be detected, evaluated and characterized. These molecular assemblies work in concert to maintain intracellular ion homeostasis. Any changes in the activity of these systems would cause a shift in the intracellular concentrations of ions and consequently to the cell metabolic response.

Ion pumps act to maintain transmembrane ion gradients utilizing ATP as a source of energy. Examples of ion pumps are: $Na^+/K^+$-ATPase maintaining transmembrane gradient of sodium and potassium ions, $Ca^{2+}$-ATPase maintaining transmembrane gradient of calcium ions and $H^+$-ATPase maintaining transmembrane gradient of protons.

Ion transporters use the electrochemical energy of transmembrane gradients of one ion species to maintain gradients of other ion counterpart. For example, the $Na^+/Ca^{2+}$-exchanger uses the chemical potential of the sodium gradient directed inward to pump out calcium ions against their chemical potential.

Ion channels, upon activation, allow for the ions to move across the cell membrane in accordance with their electrochemical potential.

Accordingly, in one embodiment of the present invention, a method as described herein is provided, wherein cellular responses are chosen from the group comprising chemically induced or physiological events in the cell including lysis, apoptosis, growth inhibition, and growth promotion; production, secretion, and surface exposure of a protein or other molecule of interest by the cell; membrane surface molecule activation including receptor activation; trans-membrane ion transports; and transcriptional regulations.

Molecules of interest which may be monitored may be any molecule of biological origin, non-limiting examples of which are peptides, polypeptides, proteins, enzymes, post-translational modified polypeptides such as lipopeptides or glycosylated peptides, antimicrobial peptides or molecules, primary or secondary metabolites such as alginates, small organic molecules, molecules having pharmaceutical properties, etc.

In a further embodiment of the present invention, a method is provided wherein said molecule of interest is selected from the group comprising peptides including lipopeptides, glycosylated peptides and antimicrobial peptides, polypeptides, proteins, enzymes, antimicrobial molecules, primary and secondary metabolites, and small organic molecules including pharmaceutical molecules.

In one embodiment of the present invention, a method is provided, wherein said test compound is a drug or any compound which might become a drug. Said test compound may be useful in the selection/validation process of a drug candidate.

Accordingly, in a further embodiment, a method is provided, wherein said test compound is a drug or any compound which is useful in the selection process of a drug candidate.

The number of possible test compounds runs into millions. Commercially available compound libraries including peptides, proteins, sugars, etc. may be obtained from, e.g., ArQule, Pharmacopeia, Graffinity, Panvera, and Oxford.

In a particular embodiment of the present invention, said test compound is a drug selected from a chemical or natural drug candidate library.

Assaying cellular responses may be done in a number of ways. Detection may be by just visual inspection; e.g. cell growth or not, cell morphology, etc. or may be by the use of detector molecules. Detector molecules may be already present in the array system; e.g. when looking at expression of a gene with a GFP reporter. Also, the detector molecules may diffuse from agar underneath the substrate as exemplified in Example 2.

Where detector molecules are not yet present in the cellular array, cellular responses may be assayed by the addition of the detector molecules to the cellular array after incubation of test-compounds with cellular components.

In one embodiment of the present invention, a method as described is provided wherein assaying of cellular responses is by:

(a) providing a detection agent to the cellular components;
(b) washing off excess of unincorporated detecting agent; and,
(c) detecting the presence or absence of a change in detectable signal, the presence of a change in detectable signal indicating a cellular response.

Alternatively, label free detection of cellular responses may be envisaged by e.g. calorimetric measurements. This allows the measurement of e.g. metabolic activities in a cell by detection with for example a sensitive IR camera.

In one embodiment of the present invention, cellular responses are assayed in whole broth or cell culture medium, in isolated cells such as pelleted cells, in supernatant of the cellular components, or in lysate of the cellular components.

In one embodiment of the present invention, detector molecules are selected from the group comprising nucleic acids including modified analogues thereof, peptides, proteins, and antibodies including antibody fragments, enzyme substrates and specific dyes. Non-limiting suitable examples of specific dyes are well known in the art and include Fluo-3, Fluo4, and Ca-dyes such as e.g. Calcium Green-1 (see e.g. Molecular Probes cataloque).

The present Invention contemplates the monitoring of more than one cellular response, by for example looking at fluorescence at different wavelengths by using e.g. CY3 and CY5 dyes, or by simultaneously employing different methods for detection.

Cells or cellular components may be modified with luminescent indicators for chemical or molecular cellular properties and may be analysed in a living state. Said indicators may be introduced into the cells before or after they are challenged with test compounds and by any one or a combination of a variety of physical methods, such as, but not limited to diffusion across the cell membrane, mechanical perturbation of the cell membrane, or genetic engineering so that they are expressed in cells under prescribed conditions. Live studies permit analysis of the physiological state of the cell as reported by the indicator during its life cycle or when contacted with a test compound such as a drug or other reactive substance.

Accordingly, in one embodiment of the present invention, providing a detection agent to the cellular components is prior to delivering of test compound thereby providing pre-labeled cellular components.

In one embodiment of the present invention, identifying the cellular responses is by luminescence.

In a further embodiment of the present invention, said luminescence is fluorescence.

Particularly useful fluorescent molecules include, by way of example and not limitation, fluorescein isothiocyanate (FITC), rhodamine, malachite green, OREGON GREEN®, TEXAS RED®, Congo red, SybrGreen, phycoerythrin, allophycocyanin, 6-carboxyfluorescein (6-FAM), 2',7'-dimethoxy-4', 5'-dichloro-6-carboxyfluorescein (JOE), 6-carboxy X-rhodamine (ROX), 6-carboxy-2',4',7',4,7-hexachlorofluorescein (HEX), 5-carboxyfluorescein (5-FAM),N,N,N',N'-tetramethyl-6-carboxyrhodamine (TAMBA), cyanine dyes (e.g. Cy5, Cy3), BODIPY® dyes (e.g. BODIPY®630/650, Alexa542, etc), green fluorescent protein (GFP), blue fluorescent protein (BFP), yellow fluorescent protein (YFP), red fluorescent protein (RFP), and the like, (see, e.g., Molecular Probes, Eugene, Oreg., USA).

Means for detecting signals in general are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with an enzyme substrate and detecting the reaction product produced by the action of the enzyme on the substrate, and calorimetric labels are detected by simply visualizing the coloured label. Further detection means are for example (micro-)calorimetry and (light)-microscopy.

Detection of cellular responses may also be accomplished by multi-step detection practices. Said practices may be, by way of example and not limitation, sandwich assays as are well-known in the art and enzymatic conversions into a detectable product.

In one embodiment of the present invention, assaying is performed in real-time.

In another embodiment of the present invention, assaying is an end-point assaying.

The methods according to the present invention can be used particularly for monitoring induced cellular responses of host cells. Induced cellular responses include but are not limited to recombination, transformation, and viral induction such as for example by temperature shift.

Accordingly, the method according to the present invention can be used particularly for on-chip recombination, transformation or viral induction of cellular components.

Additionally, the methods according to the present invention can be used particularly for functional screening of cellular responses upon assaying cellular components with test compounds.

The method and microarrays according to the present invention may further be found particularly suitable for screenings of arrays of e.g. antibiotics with mycoplasmas.

As will be well appreciated in the art, methods and microarrays according to the present invention are also particularly suitable for combinatorial screenings.

Test compound arrays may have test compounds immobilized on solid substrate surface.

It may be desirable to provide test compounds in solution at predefined regions within a substrate for screening at a later time-point. Microarrays as used in the method of the present invention are particularly suitable for the preservation of test compounds. If provided in solution, said test compounds may move freely during screenings procedures. This might be advantageous compared to affixed compound which might provoke a steric hindrance effect.

Accordingly, it is another object of the present invention to provide a microarray for performing a method according to the present invention wherein an array of test compounds is provided within predefined regions, said test compounds are in liquid solution and not immobilized in the substrate.

It is yet another object of the present invention to provide a microarray for performing a method according to the present invention wherein an array of cellular components is provided in predefined regions on a substrate, said cellular components being conditioned for preservation on said substrate.

It is yet another object of the present invention to provide a microarray for performing a method according to the present invention wherein a cellular component is provided on a substrate, said cellular component being conditioned for preservation on said substrate.

In yet a further embodiment of the present invention, a microarray according to the present invention is provided wherein said condition is chosen from the group comprising, lyophilization and glycerol dissolution.

Preserved cell arrays as described above are well suited for long-term storage. It will be well appreciated that such conditioned cellular arrays may be used as templates; i.e. as master arrays to generate subsequent secondary identical arrays by for example back-to-back printing of cellular components from the master array onto a secondary array. This handling may be repeated a number of times with the same master to create a set of secondary arrays.

In one embodiment of the invention, a microarray as described herein is provided wherein an array of detector molecules is immobilized within the substrate.

In a further embodiment of the present invention, a microarray according to the present invention is provided wherein said array of detector molecules comprises a plurality of equal detector molecules or a plurality of different detector molecules.

The present invention also encompasses the use of a microarray or solid porous substrate as described within the present specification for obtaining a low spreading of cellular component growth on the surface of the substrate. It was surprisingly found that inoculation of cellular components on the surface of the solid substrate in the methods according to the present invention leads to a limited spreading between closely packed colonies on the substrate.

It is yet another object of the invention to provide a kit for performing a method according to the present invention comprising a microarray as described herein.

SHORT DESCRIPTION OF THE FIGURES

FIG. 1 illustrates the presence of transformed colonies on a flow-through solid substrate, focusing on the edge of the substrate. The bottom panel (B) shows colonies of E. coli XL2 MRF' grown on the substrate, with nutrients diffusing through the substrate from the agar below. Upper panel (A) shows colonies grown directly on agar.

FIG. 2 illustrates the detection of β-galactosidase activity expressed by E. coli using the fluorogenic substrate MUG. Images show a 4 mm by 3 mm area and were identically scaled.

(A) Assay principle. Bacteria trapped on the surface of the flow-through solid substrate express an enzyme that forms a fluorescent product, either by the enzyme's substrate (MUG in this case) diffusing upwards to the bacteria and/or the enzyme (β-galactosidase) being released from cells diffusing downwards to the agar.

a, agar; b, flow-through substrate; c, colony (β-galactosidase)

(B) Bacteria plated on nutrient agar directly, or
(C) on a flow-through solid substrate laid on top of agar.

FIG. 3 illustrates a masked solid substrate to compartmentalize microbial growth or enzymatic reactions. Diffusion is possible from a growth medium below while lateral spreading movement of microorganisms or other materials is prevented.

(A) Schematic diagram (view from above);
(B) Picture of methanol washed masked substrate in fluorescent channel from above.

The compartments vary from 0.5 mm to 1 mm in width, 0.25 to 1 $mm^2$ in area. However, with appropriate printing technology far smaller compartments are possible.

c, compartment; dm, dividing mask on surface or penetrating through chip

FIG. 4 illustrates a masked substrate (similar to FIG. 3):
(A) substrate inoculated with E. coli expressing GFP by spreading a bacterial culture over the entire surface. Image capture was by BX41 microscope, 30 ms exposure using fluorescein filter. Compartments in this instance are approximately 0.5 to 1 mm in width. The bright areas are compartments filled with bacteria;
(B) visual illumination of a substrate inoculated with E. coli expressing GFP by touching a pipette tip into one 0.5 mm by 0.5 mm compartment;
(C) visualization of GFP under UV illumination of a substrate inoculated with E. coli expressing GFP by touching a pipette tip into one 0.5 mm by 0.5 mm compartment.

FIG. 5 illustrates filtration accumulation of bacteria on a flow-through substrate:
(A) substrate was incubated in L-broth at room temperature containing $10^3$ GFP expressing bacteria per ml and;
(B) filtration of medium through the substrate, trapping bacteria on its surface;
(C), detection of a GFP-expressing colony of E. coli (30 ms exposure) grown on flow-through substrate for 6 hours;
(D) a spot resulting from hybridization of an RNA transcript labeled with Flu to an oligo probe also on Pam-Chip array (98 ms exposure), this image is identically scaled compared to (C), spots of (c) and (D) are similar in size;
(E), (F) Comparison of typical colonies from plating GFP-expressing E. coli on L-agar (E); and colonies grown for the same length of time on the same plate on a flow-through substrate placed on the agar base (F). Magnification was identical for both pictures. The edges that define a colony boundary are invariably sharper for bacteria grown on the substrate.

FIG. 6 illustrates GFP expression as an indicator of kanamycin activity in compartmentalized flow-through chips. Error bars show standard deviation of triplicate measurements.

FIG. 7 illustrates a transformation of
(A) pUC18 (expressing ampicillin resistance but not GFP); and
(B) pGFPuv (expressing GFP protein as well as ampicillin resistance) onto compartmentalized flow-through solid substrate on L-agar plates, nt, no transformation;
(C) transformation of pGFPuv into *E. coli* by mixing cells and DNA on-chip. Microcolonies in a Pam substrate compartment are visualized by GFP fluorescence;
(D) As (A) and (B) but after 48 hours incubation with the substrate using visible illumination. It is noted that compartmentalization still contains colony spread even though inoculated compartments are confluent. The four corners have confluent bacterial growth, which has not spread to the central compartments or even partially across the masking agent.

EXAMPLES

The following examples of the invention are exemplary and should not be taken as in any way limiting.

The following experiments demonstrate the use of a flow-through substrate in living array analysis methods according to the present invention—low molecular compounds either printed on the substrate or diffusing through the substrate can be detected by a cellular response. In the following examples, the cellular responses used were of microorganisms including growth (or inhibition of growth), enzyme activity or the uptake of DNA leading to expression of a fluorescent protein. However, this does not limit the application to these areas alone, they are just illustrative of different effectors applicable to living cellular arrays. The cellular responses to effectors were assayed on the substrate, which is suitable for printing of compounds at high density for multiple parallel and miniaturized analyses.

Example 1

Provision of Transformed *E. Coli* Cells on the Surface of Porous Solid Substrate According to the present invention, the surface of the solid substrate may be contacted, by direct deposit thereon, with an inoculum of cellular components.

Ethanol-sterilized flow-through solid substrate (aluminium-oxide substrate; Anopore, Whatman) was placed on L-agar plates containing 100 µg/ml ampicillin (Sigma). 10 pg of pUC18 plasmid (Sigma) was transformed into XL2 MRF' competent cells (Stratagene, manufacturers protocols was used except only 20 µl rather than 100 µl competent cells were used per transformation) and then plated on the substrate at different dilutions, then grown for 8 hours at 37° C. and the appearance of ampicillin resistant colonies assessed. Both nutrients and ampicillin reach the bacteria from underneath the substrate through the substrate's pores.

Figure 1:
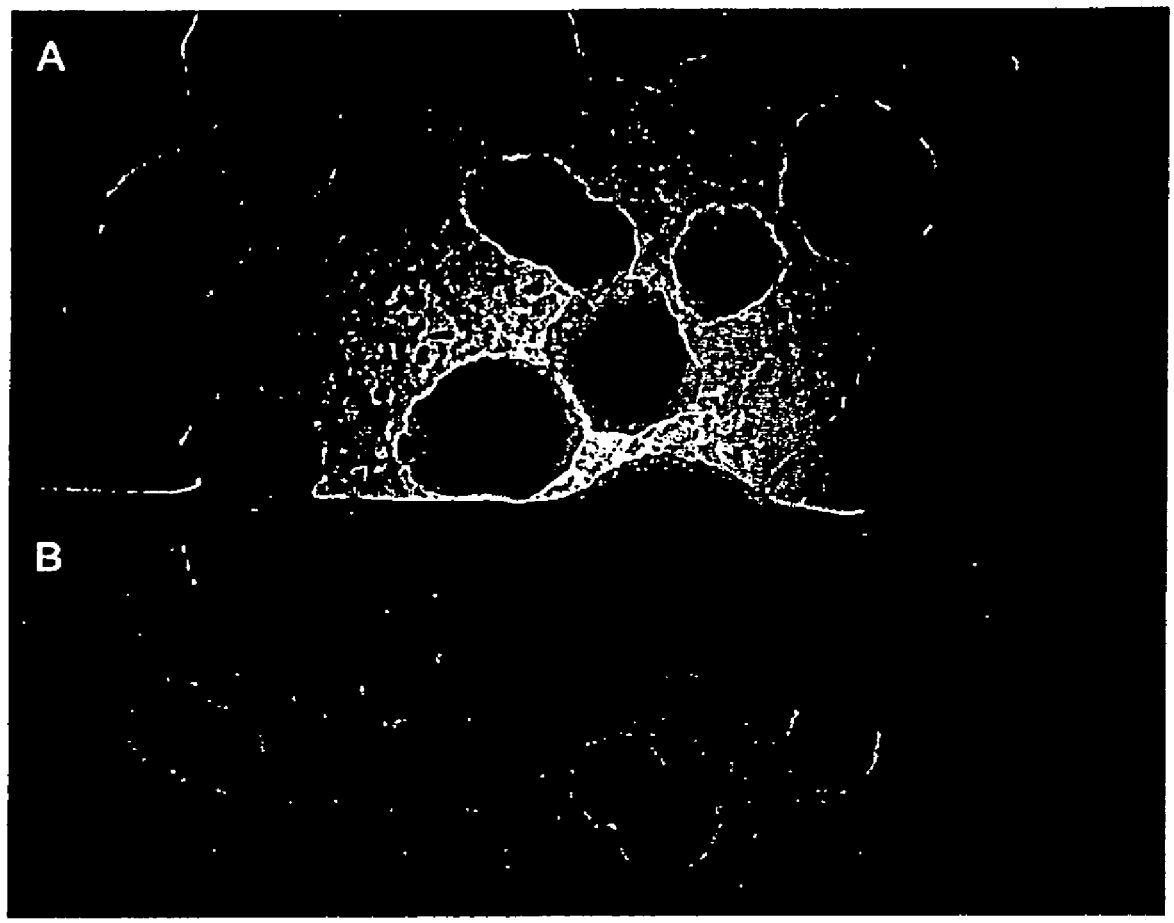

As shown in FIG. 1B, after 8 hours colonies were slightly smaller on the substrate compared to L-agar and had a reduced tendency to spread compared to colonies grown on L-agar directly (FIG. 1A). After 16 hours the colonies on the porous substrate were approximately half the diameter of those on the agar plates. Detection was by light microscopy and visual inspection. Transformation efficiencies were 2.7× $10^6$ cfu/µg plasmid (agar) and 1.8×$10^6$ cfu/µg (substrate).

These experiments show that the substrate is easily sterilized and the growth and selection of plasmid transformed cells can be performed rapidly on the surface of a porous substrate with slight lower growth efficiency. Although colony growth appears only to be marginally limited compared to direct growth on agar within the first 8 hours; after that growth appears be curtailed faster than on agar, this is an advantage in limiting spreading between closely packed colonies on the substrate, which suits this to array applications by reducing the possibility of contamination between samples.

Example 2

Figure 2:
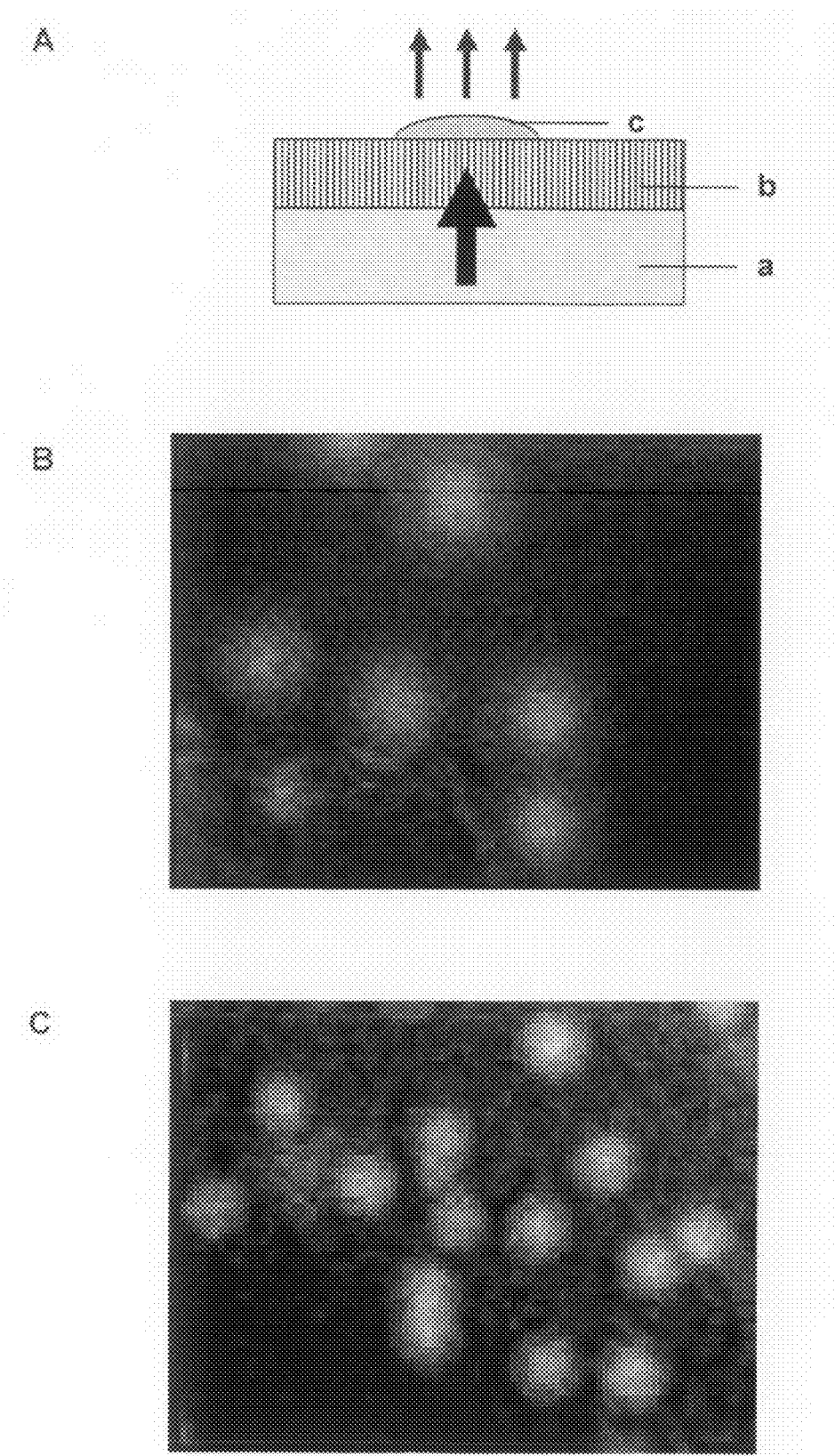

Detection of β-galactosidase Activity from *E. coli* Cells Growing on the Porous Substrate Using MUG, a Fluorogenic Substrate for this Enzyme A sterile flow-through substrate was placed on 2TY plates containing 100 µg/ml ampicillin (Sigma) and 50 µg/ml MUG (4-methylumbelliferyl p-β-galactoside, Sigma, cat: M-1633). 50 µl aliquots of L-broth containing $10^3$ cfu/ml of *E. coli* XL2 Blue MRF' with the plasmid pUC18 (expressing β-galactosidase) were plated on the substrate and a similar volume directly on agarose. Controls were performed plating the host strain lacking pUC18 on the same plates (without ampicillin). Conversion of MUG to its fluorescent product (4-methylumbelliferone) was assessed after 8 hours growth by placing the agar plates on a UV transilluminator and capturing the images of fluorescent colonies using a UVP Epi Chemi II CCD camera. FIG. 2A illustrates the experimental set up and FIGS. 2B and 2C show the results obtained on the substrate (2C) or direct on the agar (2B).

Colonies not expressing β-galactosidase were not fluorescent. Fluorescence could be detected from *E. coli* colonies containing pUC18 (and therefore expressing the enzyme) on both agar or on the substrate laid on top of the same agar plates. Fluorescence was more detectable and less diffuse on the porous substrate (FIG. 2B).

In conclusion, the methods according to the present invention allow diffusion from nutrient agar or other matrix from underneath the substrate; e.g. enzyme substrates can diffuse upwards. In addition, a suitable supported substrate with microorganisms on its surface could be moved between different media allowing sequential assays. In this experiment, by plating bacteria expressing an enzyme on porous material and the low molecular weight substrate for the enzyme in the agar underneath, the detection of bacteria based upon expression of a specific enzyme was demonstrated, in other words a phenotype based on an enzyme activity. This has many applications, e.g. in diagnostics where typing of bacteria based upon various colorimetric and fluorometric assays are common. In addition the substrate provide a low background for detection of fluorescent agents and detection was slightly enhanced on the flow-through porous material, in part reflecting less spreading of the bacteria and/or less lateral diffusion of the enzyme—a useful property for a microbial matrix which may be applied to the growth of a large number of micro-colonies in close proximity.

Example 3

Bacterial Cell Growth on the Surface of a Flow-through Solid Substrate—Sensitivity to Antibiotics Provided from Underneath the Substrate 200 nl spots of molten 0.5% agar and either 0, 500 µg/ml and 5 mg/ml kanamycin (0, 100 and 1000 ng of kanamycin) were spotted on ethanol-sterilized flow-through substrate to form 1 mm diameter agar plugs through the substrate. The porous nature of the substrate draws the molten agar into the pores by capillary action. These treated substrates were then overlaid with $10^6$ cfu/ml $E.$ $coli$ XL2 MRF' cells containing plasmid pUC18 that had been grown in 2TY broth with 100 µg/ml ampicillin and placed on 2TY plates with the same concentration of ampicillin. Plates were then incubated for 12 hours at 37° C. The results are shown in Table 1.

In conclusion, this experiment shows that antibiotic sensitivity can be tested on a micro scale by printing agar plugs containing an antibiotic on the porous substrate. The living array according to the present invention allows the localization of effectors in controlled spots either printed directly or embedded in a matrix such as low melting point agarose within the pores of the porous substrate. Printing the antibiotic directly, or in agar, or other matrix, may allow this assay to be multiplexed so that thousands of assays may be performed per square centimetre of array surface with a precision and lack of cross-contamination not possible on glass or other planar arrays.

Example 4

Trapping of Bacteria on the Surface of a Flow-through Solid Substrate by Filtration—Colony Detection and Morphology $E.$ $coli$ XL2 blue MRF' cells containing the plasmid pGF-Puv (Clontech/BD) and actively expressing GFP were diluted to $10^3$ bacteria/ml. Sterile flow-through substrate was placed in a 0.22 µM pore, 10 cm diameter Nalgene filter and medium drawn over and through the substrate. As a control, substrate was incubated with shaking in a similar volume of medium with the same density of bacteria. The substrate was then incubated on L-agar plates overnight and GFP used to visualize colonies.

Figure 5:
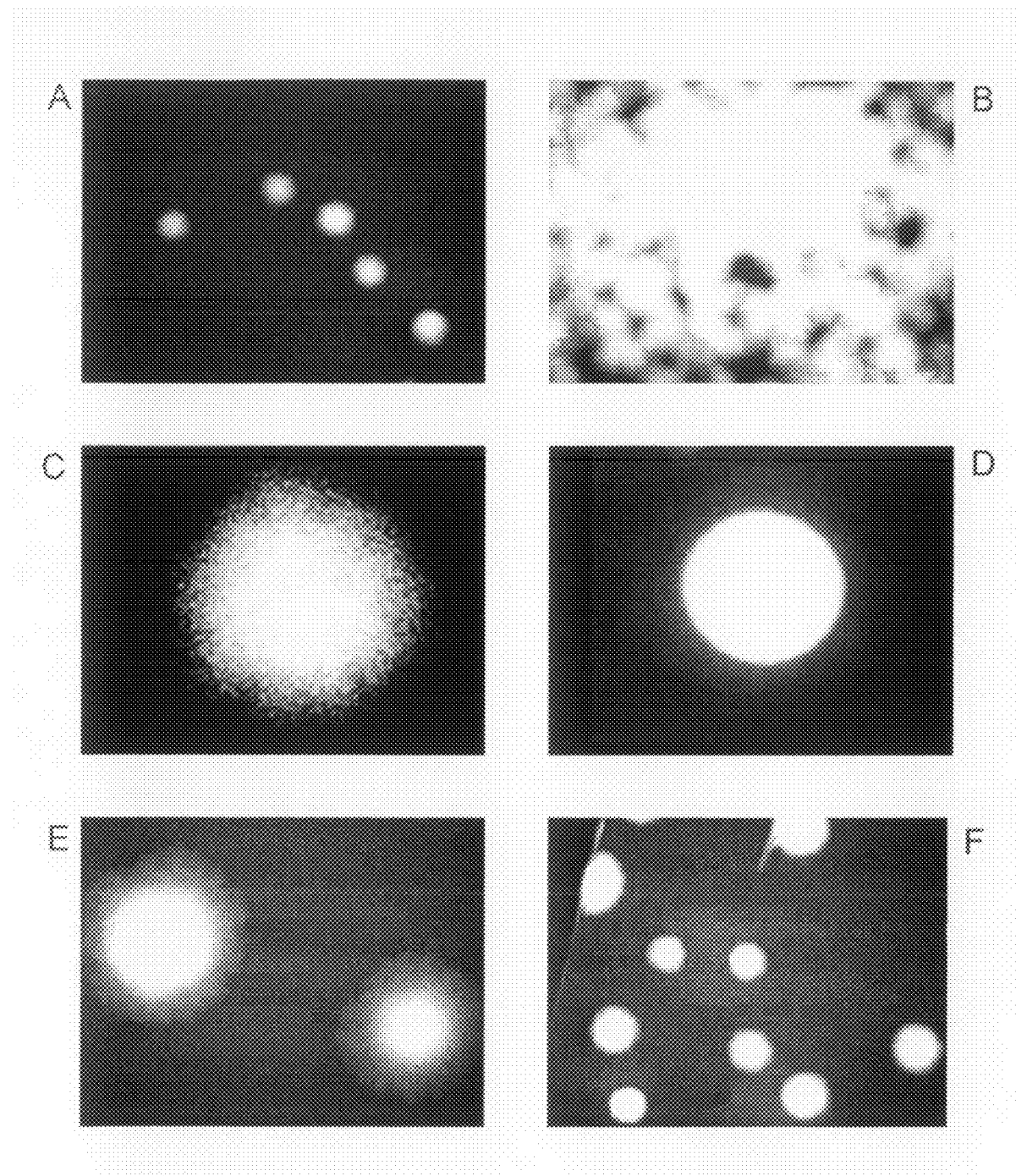

As shown in FIGS. 5A and 5B, accumulation of bacteria was demonstrated. In addition micro-colonies could be detected that were below 100 µm in diameter on the substrate (FIGS. 5C and 5D); bacterial colonies (FIG. 5C) could be detected at the same size as a printed oligonucleotide spot (FIG. 5D).

In conclusion, concentrating bacteria by trapping them by filtration using an appropriately supported flow-through substrate was demonstrated. In general, microorganisms are not allowed to penetrate the agar or other matrix underneath the substrate. This is applicable to applications such as water quality testing, for example a combination of filter enrichment and on an array substrate spotted with selective growth media or a further capture or typing agent (e.g. antibody). In addition, as has been seen in other experiments, bacterial colonies spread less on the flow-through substrate compared to agar and can be detected at the same size as a printed oligonucleotide spot These last two properties support the use of the flow-through substrate in high-density living array applications.

Example 5

Use of a Superposing Mask on the Flow-through Solid Substrate—Compartmentalization and Autofluorescence Testing As demonstrated in the above experiments, the flow-through solid substrate as used in the present invention shows relatively low spread of microorganisms on its surface, however it may still be desirable to compartmentalize it further for enzymatic reactions or microbiology or other living cell array applications.

Ethanol sterilized flow-through solid substrate was painted with a variety of compounds to look for a suitable masking agent to compartmentalize regions of the substrate. Criteria for a suitable masking agent were (1) easy to apply, (2) low fluorescence in Cy3, Cy5 and fluorescein channels, (3) resistant to solvent sterilization, (4) not water soluble and (5) capable of blocking both the pores in the substrate and preventing microbial spread within discrete areas (see FIG. 3A). The lead candidate, a latex masking film, was tested extensively for suitability in terms of sterility, solvent resistance, autofluorescence and ease of application.

Figure 3:
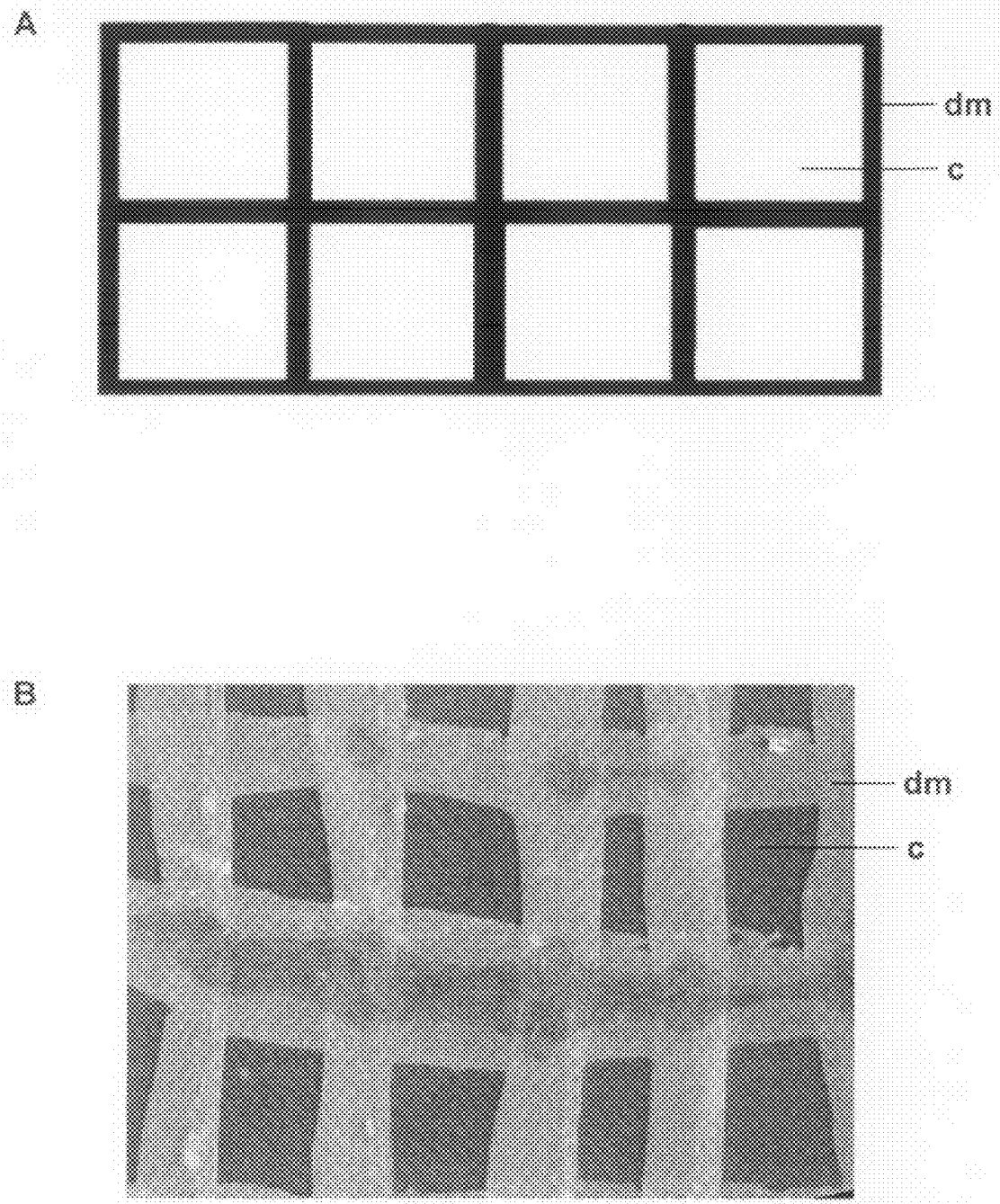

An appropriate substance was found to be latex liquid masking film with low fluorescence as sold by art suppliers. Talens Liquid Masking Film (052, Royal Talens, Apeldoorn, Holland) was suitable but other masking agents may be equally applicable. The masking agent was applied using an ethanol-sterilized number 1 sable brush. After allowing 2 hours to dry, samples were immersed in 95% ethanol, 100% methanol, 100% isopropanol, sterile 1% SDS, sterile water or 100% DMSO for 10 minutes, then rinsing in sterile water and drying. Treated substrate was then assessed for resistance of the masking fluid to solvents, fluorescence, and sterility (see Table 2). An example of masking is shown in FIG. 3 B.

In conclusion, the surface of the flow-through substrate can be compartmentalized for microorganisms using a printed masking agent that also turns the substrate into a more robust composite material. Even after conditions that would lead to over-growth on agar, compartmentalization is effective on the flow-through substrate.

The wash step had a moderate effect on fluorescence of the masking agent but did not affect sterility. Methanol and DMSO appeared to be the best washing agents as they left the substrate and masking agent undamaged and with a low autofluorescence. Once dry, the masking agent was extremely resistant to the solvents tested. This mask is intended to compartmentalize the living array, with a different analyte or cell-type applied to each compartment and is most applicable to growth on a solid substrate suiting bacterial and fungal applications but may also be used to reduce lateral spread of mammalian or other surface-grown tissue culture cells.

Example 6

Masking Areas of the Flow-through Substrate—Compartmentalization for Bacterial Growth Flow-through substrate was sterilized, masked as above and washed in 100% methanol before use. The substrate was then placed on L-agar plates containing 100 µg/ml ampicillin and 1 mM IPTG and either overlaid or spotted with *E. coli* XL2 blue MRF' containing plasmid pGFPuv (Clontech/BD Biosciences) expressing a variant GFP suited to bacteria. Growth and fluorescent was assessed after incubation overnight at 37° C.

Figure 4:
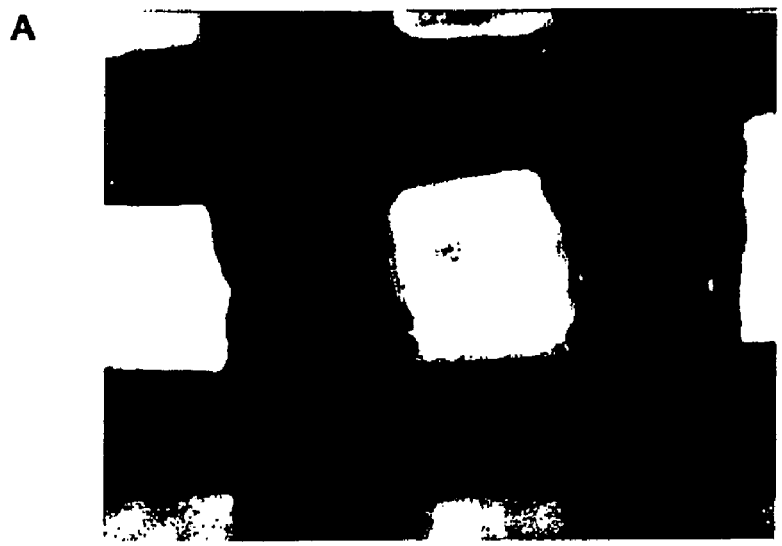
Figure 4:
Figure 4:
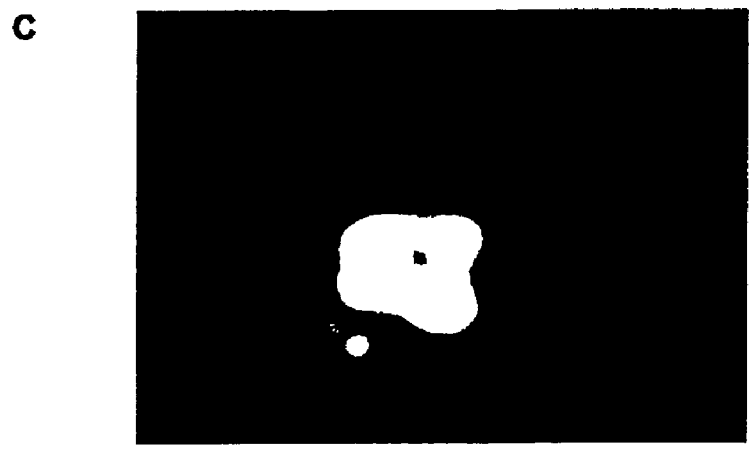

As shown in FIG. 4A, good growth was observed in the case of specific spotting into compartments, good containment of bacteria without spreading to adjacent compartments was demonstrated (FIGS. 4B and 4C).

In conclusion, bacterial growth can be compartmentalized effectively with no spreading between compartments using a masking agent. Automated printing and masking may allow further miniaturization of this process.

Example 7

Use of GFP Expression to Monitor Antibiotic Sensitivity on Compartmentalized Flow-through Substrate Compartments of flow-through substrate were printed in 1% Metaphor agarose containing various concentrations of kanamycin. Care was taken to print at a temperature below 60° C. and all samples were printed in triplicate. These substrates were placed on L-agar plates containing 100 µg/ml ampicillin and overlaid with *E. coli* XL2 Blue expressing GFP. A microscope equipped with a Kappa camera was used to capture images, which were digitized and quantified to assess the effect of kanamycin on bacterial growth and viability.

Figure 6:
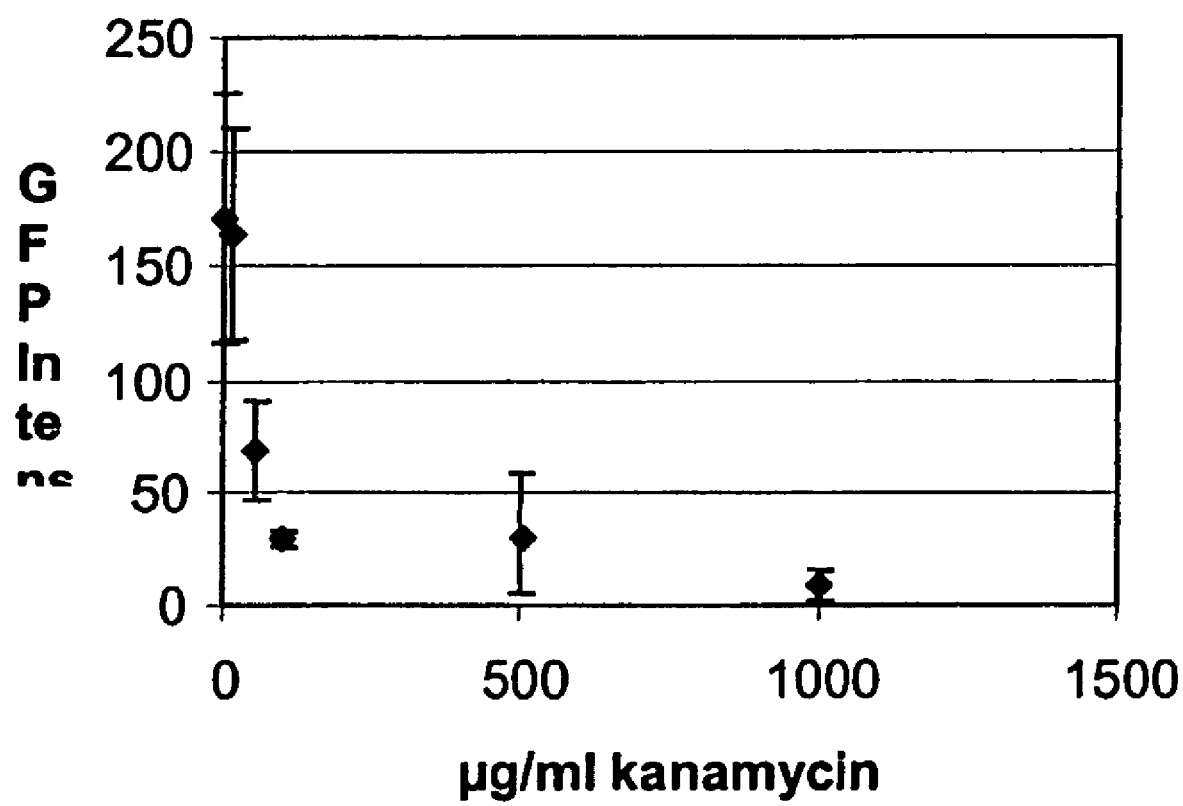

The effect of kanamycin on viability could dearly be detected using a GFP reporter as shown in FIG. 6.

In conclusion, this experiment demonstrates the use of a fluorescent reporter or readout system being used in living arrays on a flow-through substrate.

Example 8

Transformation of Plasmids into *E. coli* on Compartmentalized Flow-through Substrate Two methods were used, the first, (a) mixes plasmid and *E. coli* immediately before application to the array and the second, (b) mixes the two components on the array itself.

(A) 10 ng of pGFPuv or pUC18 were transformed separately into 10 µl aliquots of competent cells (Stratagene XL2 Blue MRF') simply by mixing the two components, and these mixes were spotted in 0.2 µl (approx) aliquots in compartmentalized flow-through chips which were then cultured on L-agar/ampicillin plates overnight.

(B) pGFPuv DNA (approx 0.2 µl) was spotted on substrate, then 0.5 µl competent cells were spotted on a few seconds later. Substrate was then placed on and incubated on L-agar/ampicillin plates overnight.

Figure 7:
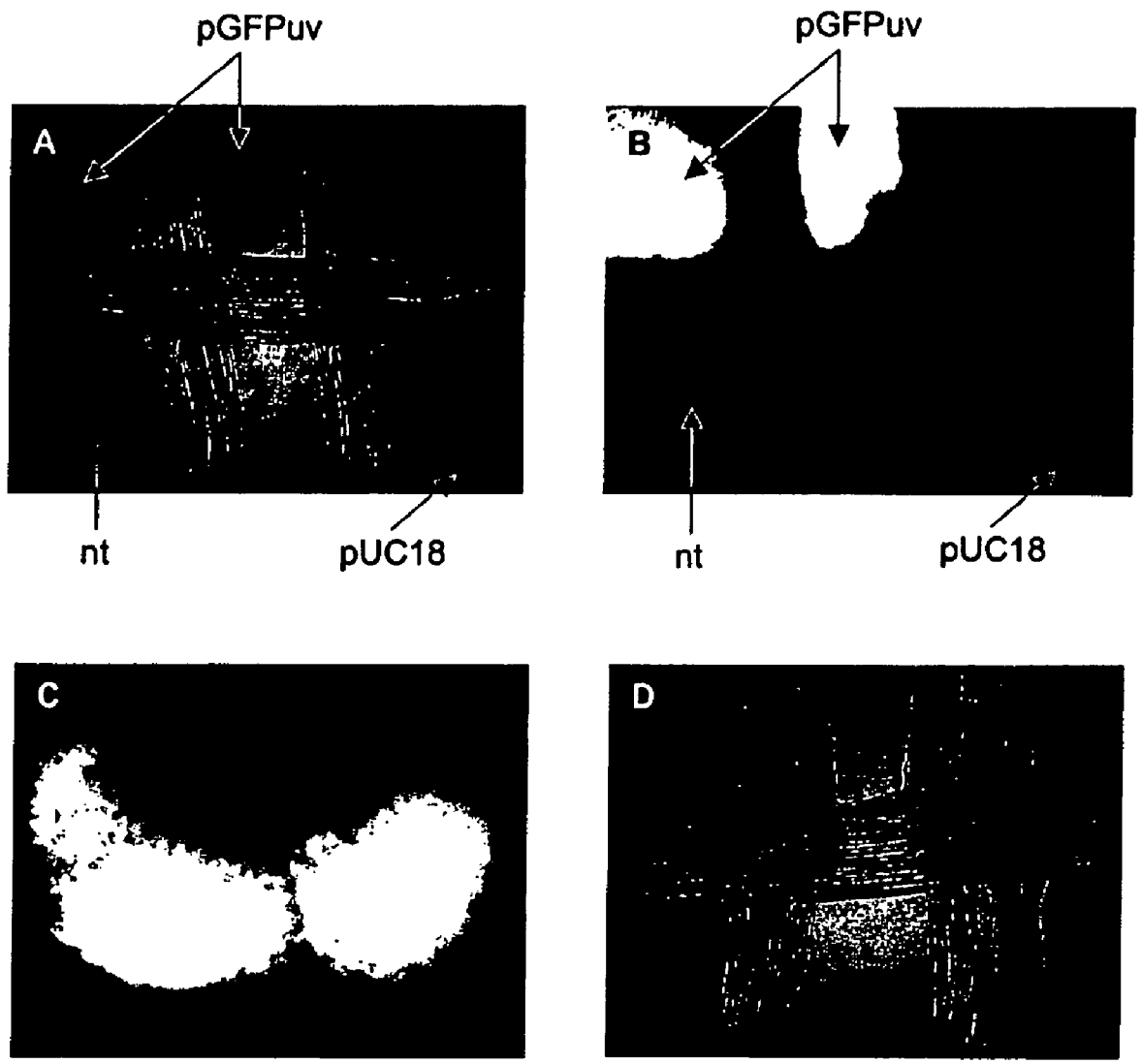

As shown in FIGS. 7A and 7B, pUC and pGFPuv could be transformed onto compartmentalized substrate efficiently after a brief premixing according to the above-mentioned method A. No spreading to adjacent compartments was observed.

As shown in FIG. 7C, pGFPuv could also be transformed into *E. coli* by mixing the two components on the substrate according to the above-mentioned method B.

In conclusion, compartmentalization is effective even after 48 hours (FIG. 7D) in containing the growth of inoculated regions and preventing cross-contamination. These data on transformation opens the way to transformation methods that involve spotting of purified DNA followed by the introduction of cells directly onto the substrate together in rapid succession or together for living array applications. Bacteria can be transformed immediately prior to printing or even on-chip with high efficiency.

Chilled incubation of bacteria with DNA and heat shock common in many transformation protocols may also be performed on chip. It is potentially possible to print, for example, 96 cells types (e.g. *E coli* with 96 different transposon insertions) from one set of 96 well plates with 96 complementing plasmids (or other effector taken up from the substrate) for thousands of combinations of strain and effector using this methodology.

Example 9

Antibody Capture of Bacteria on Flow-through Substrate

Untreated flow-through substrate was ethanol-sterilized then treated with aliquots of Rabbit anti-*E. coli*, Ig fraction, raised by inoculation of a Rabbit with a sonicated extract of the *E. coli* K12-derived strain C600 (from DAKO A/S Denmark, CATB0357, lot 090-101) or control antibody (M13 antibody from Santa Cruz). These slides were incubated in a humidity chamber for 2 hours then briefly dried to immobilize the antibodies, washed and incubated with 10 ml L-broth with $10^6$ *E. coli* expressing GFP with gentle shaking (or sterility control, without *E. coli*). After washing in L-broth the substrates were plated on L-agar plates and fluorescent colonies counted the next day.

Figure 8:
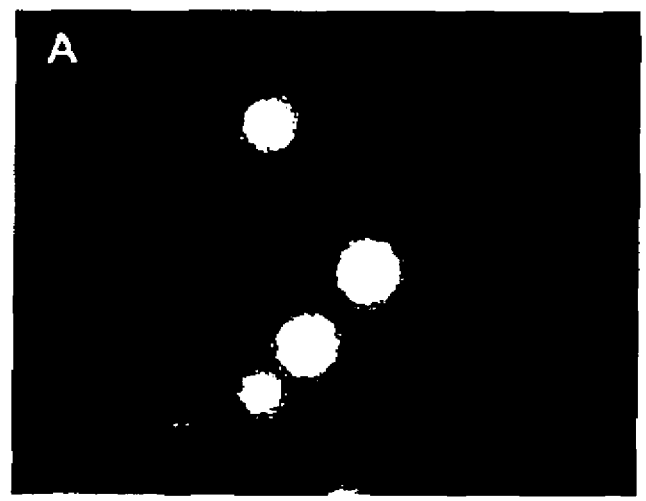
FIG. 8 illustrates antibody capture of *E. coli* visualized by GFP expression:
(A) M13 antibody (negative control);
(B) *E. Coli* antibody (raised against whole cell extracts).
Figure 8:

As a result, accumulation of bacteria specific to the *E. coli*-specific antibody was observed as shown in FIG. 8. An average of 214 colonies per substrate (n=2) was observed with *E. coli* antibody and 71 with M13 control antibody (n=2).

In conclusion, specific antibody capture of cells was demonstrated on the flow-through substrate.

Example 10

Antibody Arrays

Antibodies against the heat shock proteins HSP90alpha, HSP90beta, PolyUBQ and beta-actin are spotted in an array format on an aluminium-oxide substrate (Anopore, Whatman) using standard protocols Jurkat cells are grown under standard conditions in a $CO_2$ incubator to a density of $10^6$ cells/ml. 25 µl of cell suspension is added to the array. The culture medium is removed by suction through the array using the standard equipment, and 50 µl of fresh medium is added. The cells are incubated under sterile conditions at 37° C. on the substrate for 24 hrs, or till a density of $10^7$ cells/ml is reached. The temperature is raised to 43° C. for 15 min. The control is kept at 37° C. The culture medium is removed by suction through the array. The cells are washed with 50 µl wash liquid. After removal of this liquid by suction through the array, 25 µl lysis buffer is added. After 15 min of lysis, the liquid is pumped back and forth through the array for 15 min with two cycles, of up and down flow, per minute. The liquid is removed by suction, the array is washed with 25 µl of wash buffer, which is removed by suction. 20 µl of a mixture of anti-heatshock antibodies (anti-HSP90alpha, anti-HSP90beta, anti-PolyUBQ and anti-beta-actin, all labeled with fluorescein), is added and pumped through the array for 15 minutes at two cycles per minute. Images are captured every two minutes. In the case the background is too high, the antibody solution is removed from the array and the array is washed with wash buffer. Images are taken. Data will be analysed using standard software.

Antibodies may be monoclonals, polyclonals, single chain antibodies, aptamers whereby those spotted on the substrate recognize another epitope than those added for detection of bound antibodies.

Example 11

Induction of Cytochrome P450 Isoenzyme 1A (CYP1A)

Ethoxyresorufin is chemically modified with a crosslinker and spotted on an aluminium-oxide substrate using spotting technology as is well known in the art.

Hepatocytes are prepared as described by van 't Hoen et al. (2000). P. A. Chr 't Hoen et al. Selective induction of cytochrome P450 3A1 by dexamethason in cultured rat hepatocytes. Analysis with a novel reverse transcriptase-polymerase chain reaction assay. Biochemical Pharmacology, Vol. 60 pp 1509-1518 (2000). Viability is judged by tryptan blue exclusion. 50 µl of cell suspension at a cell density of 80000 cells/ml is added to the substrate. The culture medium is removed by suction through the substrate using standard equipment. To allow adherence, the cells are initially cultured for 3.5 hr in DMEM containing 10% (v/V fetal calf serum, 140 mU ml$^{-1}$ insulin, 2 mM L-glutamine, 100 U ml$^{-1}$ penicillin, and 100 microgram ml$^{-1}$ streptomycin in a humidified $CO_2$ atmosphere at 37° C. Thereafter, non-adhering cells are washed away by pipetting the medium away. The incubation medium is changed to serum-free DMEM, containing 0.2% (w/.v) BSA, 140 mU ml$^{-1}$ insulin, 2 mM L-glutamine, 200 U ml$^{-1}$ penicillin, and 200 microgram ml$^{-1}$ streptomycin. The hepatocytes will form a confluent layer within 1 day. Twenty-four hrs after application of the cells to the array, most of the medium is removed by suction, taking care not to dry the cells.

Benzo[a]pyrene, dexamethasone, phenobarbital, hexobarbital, debrisquine, aniline, midazolam (concentration ranging from 1 to 100 µM in DMSO) are applied on specific locations (arrayed) onto the cell layer with piezo inkjet spotting technology. Thirty min after application of the inducers, 25 microliter of culture medium is added.

At different time points the medium is removed by suction and 5 µl lysis buffer is added. Two µl of a reaction solution is added and the lysate is pulled into the array. Development of fluorescence by liberation of resorufin in the pores is monitored using the standard equipment, and capturing images every 10 sec.

These compounds induce different isoenzymes of cytochrome c. Some are very active in converting ethoxyresorufin, others hardly or not at all. By lysis, cyt P450 should diffuse out of the cell, but this may be difficult since it is a membrane bound enzyme that may need coenzymes and cofactors.

Alternatively, it may not be necessary to couple ethoxyresorufin to the substrate, addition and uptake by the cells may allow monitoring of activity in situ, before it diffuses away.

During this enzymatic reaction no pumping is done to prevent the product from diffusing away from the reaction site.

Example 12

Growth of a Filamentous Fungi on Flow-through Substrate

A *Penicillium* species fungi isolated from stale bread was plated on a flow-through substrate (aluminium oxide; Anopore; Whatman) on L-agar and incubated in a humidity chamber for 3 days at room temperature.

Figure 9:
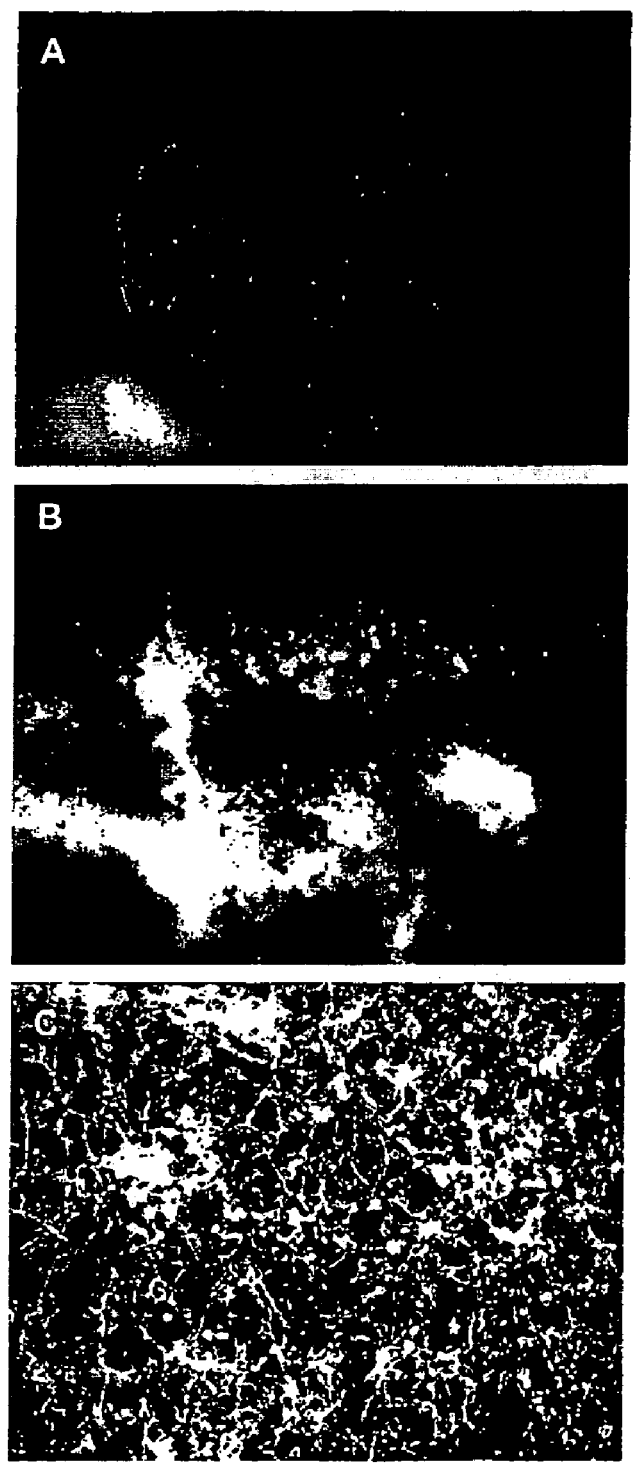
FIG. 9 illustrates the growth of a *Penicillium* isolate on a flow-through solid substrate:
(A) parental strain growing on bread;
(B) Mycelium growing immediately on the substrate surface;
(C) aerial Mycelium growing 3 mm above substrate surface from the same experiment as (B), picture focuses on mycelium originating on the substrate but projecting significantly above it.

Good and rapid growth was obtained as shown in FIGS. 9A, 9B and 9C.

This experiment demonstrates that fungal growth is possible on the flow-through substrate, a similar range of applications may be possible in living chips as for prokaryotic microorganisms.

Example 13

Principles of Antibody Capture and On-Chip Detection Based on Detergent Sensitivity, Enzyme Activity and a Transposon Insertion in a Strain Typing, Diagnostic Setting for a Bacterial Pathogen The principles of antibody capture and on-chip detection based on detergent sensitivity, enzyme activity and a transposon insertion in a strain typing, diagnostic setting for a bacterial pathogen are illustrated. In this analysis, a great deal of information is obtained from only a 5-spot array. The experiment assumes a mixture of nine bacterial strains obtained from a patient (Table 3) and a five-spot antibody array format representing antibodies to antigens A, B, C, D, E respectively (FIG. 10); spot E is a negative control spot.

Figure 10:
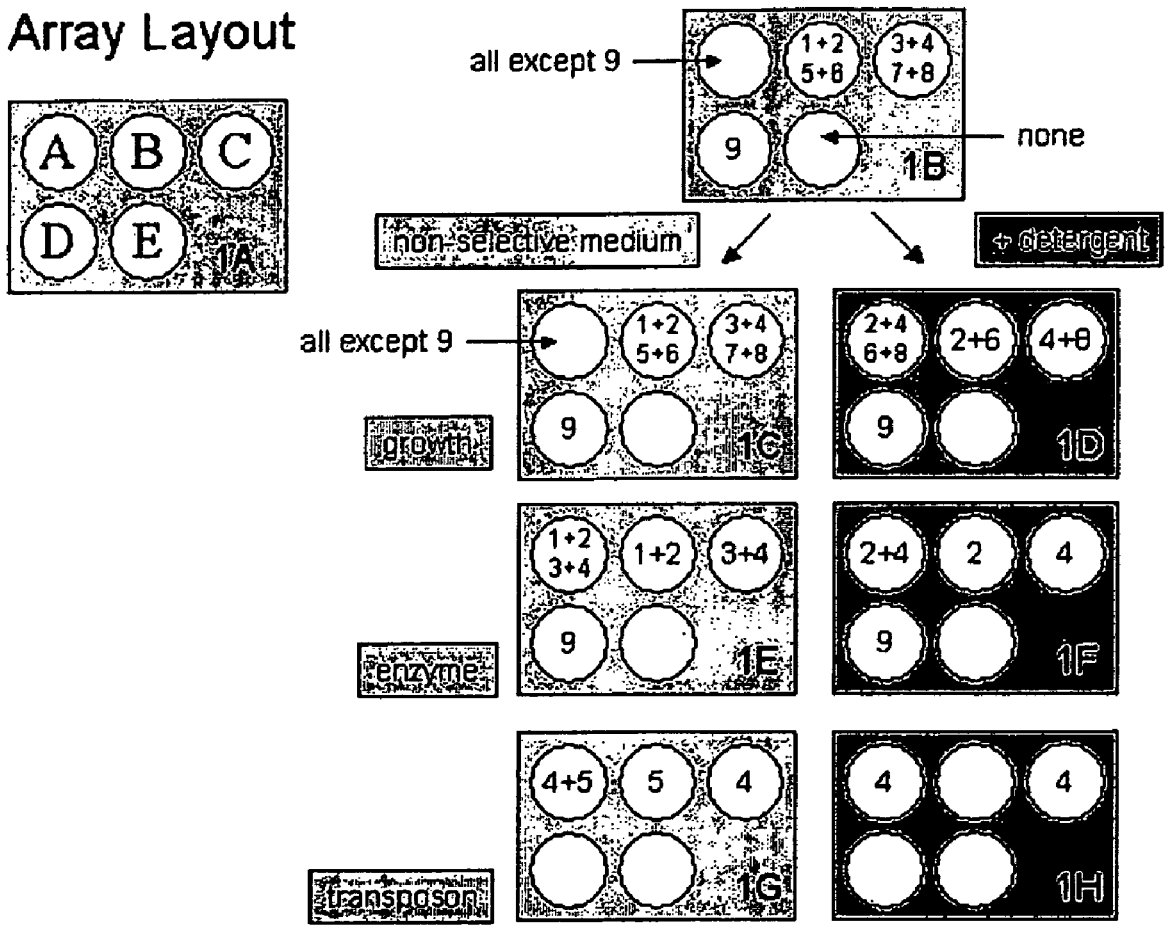
FIG. 10 illustrates the principles of antibody capture and on-chip detection based on detergent sensitivity, enzyme activity and a transposon insertion in a strain typing, diagnostic setting for a bacterial pathogen.

A complex sample of pathogenic bacteria from a patient is passed through two identical arrays, as described in FIG. 10—array 1A. The expected recruitment of each strain type to the array, based on surface antigens A to D captured by specific antibodies is shown in FIG. 10—array 1B. The numbers in each spot indicate the strains recruited to each position on the array.

The first array is then placed on an unselective agar medium on which all strains should grow. The second array is plated on a selective medium containing a detergent that inhibits the growth of detergent-sensitive strains. The expected patterns of growth (which spots turn into colonies from nutrients diffusing upwards through the porous Pam substrate) are shown in FIG. 10—arrays 1C and 1D.

The arrays 1C and 1D are now plated on another medium containing a fluorogenic substrate for the enzyme of interest. The colonies predicted to become fluorescent due to enzyme activity are shown in FIG. 10—arrays 1E and 1F. This requires capture of the appropriate strain, growth on a selective medium and production of the enzyme in question.

The arrays are then removed from the selective agar, and the cells on the array lysed in situ, their DNA cross-linked to the substrate. Then, standard nucleic acid hybridization is performed, using the functionality of the flow-through array as a rapid hybridization array, with a labelled oligonucleotide that detects transposon X by specific hybridization. The expected results are shown in FIG. 10—arrays 1G and 1H.

Now, only strains that are captured by a specific antibody, are able to grow on the medium used and contain the transposon sequence are detected.

This array system gives great flexibility and the possibility of combining many different assays towards a complex analysis of multiple parameters simultaneously.

TABLE 1

Sensitivity of *E. coli* XL2 Blue MRF' to the antibiotic kanamycin when cultured on the Pam substrate.

| Kanamycin (ng) | Zone of clearing (diameter mm) | Replicates (N) | Standard Deviation |
|---|---|---|---|
| None | 0 | 12 | na |
| 10 | 0.4 | 12 | 0.3 |
| 100 | 2.1 | 16 | 0.3 |
| 1000 | 3.5 | 12 | 0.3 |

TABLE 2

Effect of washing treatment on the masking agent applied to the Pam substrate.

| Treatment | Flu | Cy3 | Cy5 | Solvent resistance | Sterility |
|---|---|---|---|---|---|
| Ethanol | + | + | +/− | good | yes |
| Methanol | +/− | +/− | − | good | yes |
| DMSO | +/− | +/− | − | good | yes |
| Water | + | ++ | +/− | good | yes |
| SDS | + | + | +/− | good | yes |
| Isopropanol | + | + | +/− | good | yes |

Fluorescence: Assessed using Olympus BX41 UV microscope. ++ unacceptably high auto-fluorescence (saturates below 98 ms exposure), + saturates 12-bit Kappa CCD camera between 98 and 200 ms exposure, +/− saturates CCD camera between 200 ms and 1 second. − saturates CCD camera above 1 second exposure.

Solvent Resistance: Assessed using light microscopy using BX41 camera, assessed on the basis of resistance of the masking agent to the washing treatment.

Sterility: Assessed by plating substrate on L-agar plates at 37° C. overnight. Sterile indicates no colonies on substrate surface.

TABLE 3

Nine bacterial strains in a patient's sample as used in Example 13. Only strains 4 and 5 have transposon X inserted in their genome

| Strain No. | Enzyme activity | Surface antigen | Detergent sensitivity |
|---|---|---|---|
| 1 | Positive | A and B | Sensitive |
| 2 | Positive | A and B | Insensitive |
| 3 | Positive | A and C | Sensitive |
| 4 | Positive | A and C | Insensitive |
| 5 | Negative | A and B | Sensitive |
| 6 | Negative | A and B | Insensitive |
| 7 | Negative | A and C | Sensitive |
| 8 | Negative | A and C | Insensitive |
| 9 | Positive | D | Insensitive |

The invention claimed is:

1. A method for screening of responses of viruses, cells or cellular components thereof comprising:
    (a) providing cells or cellular components on the surface of a solid porous metallo-oxide substrate, wherein said cells or cellular components are mammalian cells, insect cells, yeast cells, fungal cells, plant cells, bacteria, viruses or components thereof, and wherein
        (i) said solid porous substrate has oriented through-going channels;
        (ii) said solid porous substrate retains said cells or cellular components on the substrate surface, and wherein,
        (iii) said solid porous substrate has immobilized therein, within the pores, an array of detector molecules, wherein said detector molecules are nucleic acids, peptides, proteins, antibodies, antibody fragments, enzyme substrates or specific dyes and wherein said detector molecules are appropriate to detect cellular responses to be assayed;
    (b) delivering test compounds to positions on the substrate corresponding to the arrayed detector molecules on the surface of said solid porous substrate;
    (c) incubating said test compounds with said viruses cells or cellular components on the surface of the solid porous substrate, under conditions allowing the induction of responses, wherein said responses are chemically-induced or physiological events in said cells; production, secretion or surface exposure of a molecule of interest by said cells; membrane surface molecule activation; receptor activation; transmembrane ion transports; or transcriptional regulations;
    (d) assaying said responses, wherein responses are detected using said detector molecules; and, identifying and characterizing the responses induced by said test compounds.

2. The method according to claim 1, wherein said solid substrate is a flow-through porous solid substrate.

3. The method according to claim 1, wherein said providing of viruses cells or cellular components on the surface of a substrate is by a deposit directly on said substrate of an inoculum or a culture.

4. The method according to claim 1, wherein said delivering of test compounds is by means of contact force.

5. The method according to claim 4, wherein said contact force is a capillary force or a piezo-electric-force.

6. The method according to claim 1, wherein nutrient(s) are provided from underneath the pores of the solid surface.

7. A method for screening of responses of viruses, cells or cellular components comprising:
    (a) providing cells or cellular components on the surface of a solid porous metallo-oxide substrate, wherein said cells or cellular components are mammalian cells, insect cells, yeast cells, fungal cells, plant cells, bacteria, viruses or components thereof, and wherein
        (i) said solid porous substrate has oriented through-going channels, and
        (ii) said solid porous substrate retains said cells or cellular components on its surface;
    (b) incubating test compounds with said cells or cellular components on the surface of the solid porous substrate, under conditions allowing the induction of responses, wherein said responses are chemically-induced or physiological events in said cells; production, secretion or surface exposure of a molecule of interest by said cells; membrane surface molecule activation; receptor activation; transmembrane ion transports; or transcriptional regulations; and
    (c) assaying said responses by
        (i) providing a detector molecule to the cells or cellular components;
        (ii) washing off excess of unincorporated detector molecule; and
        (ii) detecting the presence or absence of a change in a detectable signal from the detector molecule, the presence of a change in detectable signal indicating a response; wherein said detector molecule is a nucleic acid, peptide, protein, antibody, antibody fragment, enzyme substrate or specific dye.

8. The method according to claim 7, wherein said providing a detector molecule to the viruses, cells or cellular components occurs prior to delivering of test compound thereby providing pre-labeled viruses, cells or cellular components.

9. The method according to claim 1, wherein said response is assayed in whole broth or cell culture medium, in isolated cells such as pelleted cells, in supernatant of the cells or cellular components, or in lysate of the cells.

10. The method according to claim 1, wherein said delivery of test compounds is by a means selected from the group consisting of a delivery mask, a high precision x-y-z pipettor, inkjet printer, and manual handling.

11. The method according to claim 10, wherein said delivery of test compounds is by means of a high precision x-y-z pipettor or inkjet printer.

12. The method according to claim 1, wherein said identifying of the cellular responses is by luminescence.

13. The method according to claim 12, wherein said luminescence is fluorescence.

14. The method according to claim 1, wherein said cellular components are, cellular vesicles or cellular organelles.

15. The method according to claim 1, wherein said detector molecules are specific dyes.

16. The method according to claim 1, wherein said responses are chosen from the group consisting of chemically induced or physiological events in the cell selected from the group consisting of lysis, apoptosis, growth inhibition, and growth promotion.

17. The method according to claim 1, wherein said molecule of interest is selected from the group consisting of peptides, lipopeptides, glycosylated peptides, polypeptides, proteins, enzymes, antimicrobial molecules, and primary and secondary metabolites.

18. The method according to claim 1, wherein said test compound is a drug or a compound which is useful in the selection process of a drug candidate.

19. The method according to claim 18, wherein said test compound is a drug selected from a chemical or natural drug candidate library.

20. The method according to claim 1, wherein said solid porous substrate is an aluminum-oxide substrate.

21. The method according to claim 1, wherein said assaying is performed in real-time.

22. The method according to claim 1, wherein said assaying is an end-point assaying.

23. The method of claim 1, wherein viruses, cells or cellular components are provided using on-chip recombination, transformation or viral introduction.

24. The method of claim 1, wherein an array of detector molecules is provided within the pores of said substrate, and wherein an array of test compounds is provided within predefined regions, wherein said test compounds are in liquid solution and not immobilized in the substrate.

25. The method of claim 1, wherein an array of detector molecules is provided within the pores of said substrate, and wherein an array of cells or cellular components is provided in predefined regions on a substrate, said cells or cellular components being conditioned for preservation on said substrate.

26. The method of claim 1, wherein an array of detector molecules is provided within the pores of said substrate, and wherein a cellular component is provided on a substrate, said cellular component being conditioned for preservation on said substrate.

27. The method according to any of claims 24 to 26, wherein said array of detector molecules comprises a plurality of the same detector molecules or a plurality of different detector molecules.

28. The method according to claim 25 or 26, wherein said conditioning is chosen from the group consisting of lyophilization and glycerol dissolution.

29. The method according to claim 1, wherein the viruses, cells or cellular components on the surface of the substrate comprise viruses, cells or cellular components with low spreading properties.

30. The method according to claim 1, wherein said cells or cellular components are bacterial cells or components thereof.

31. The method of claim 1, wherein said test compounds are small organic molecules or pharmaceutical molecules.

* * * * *